United States Patent
Sakamoto et al.

(10) Patent No.: US 10,535,135 B2
(45) Date of Patent: Jan. 14, 2020

(54) IMAGE PROCESSING APPARATUS, CONTROL METHOD THEREOF, AND STORAGE MEDIUM

(71) Applicant: CANON KABUSHIKI KAISHA, Tokyo (JP)

(72) Inventors: Tsuyoshi Sakamoto, Tokyo (JP); Yusuke Imasugi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 153 days.

(21) Appl. No.: 15/336,238

(22) Filed: Oct. 27, 2016

(65) Prior Publication Data
US 2017/0124705 A1    May 4, 2017

(30) Foreign Application Priority Data
Oct. 29, 2015 (JP) .................... 2015-213476
Sep. 30, 2016 (JP) .................... 2016-192784

(51) Int. Cl.
G06K 9/00 (2006.01)
G06T 7/00 (2017.01)
A61B 6/00 (2006.01)

(52) U.S. Cl.
CPC .............. *G06T 7/0012* (2013.01); *A61B 6/50* (2013.01); *G06T 2207/10081* (2013.01); *G06T 2207/30061* (2013.01)

(58) Field of Classification Search
None
See application file for complete search history.

(56) References Cited

U.S. PATENT DOCUMENTS

| 2011/0190626 A1* | 8/2011 | Mizuno ................. G06T 7/0012 600/425 |
| 2013/0331725 A1* | 12/2013 | Noji ..................... A61B 6/5217 600/534 |
| 2015/0317452 A1* | 11/2015 | Kozuka ................ G06F 19/321 705/2 |

FOREIGN PATENT DOCUMENTS

JP    2003-70781 A    3/2003

OTHER PUBLICATIONS

Guidelines for the diagnosis and treatment of COPD (chronic obstructive pulmonary disease), 2nd ed., The Japanese Respiratory Society, Medical Review Co. Ltd. (2004), pp. 12, 13.

* cited by examiner

*Primary Examiner* — Stephen P Coleman
(74) *Attorney, Agent, or Firm* — Canon U.S.A., Inc., IP Division (57) ABSTRACT

Medical image data is identified, and a lung field region and an emphysema region in each of a plurality of tomographic images are extracted. A mechanism is provided, which is capable of calculating the ratio of the emphysema region to the lung field region, and displaying an image of the medical image data and a value representing the calculated ratio in association with each other.

20 Claims, 8 Drawing Sheets

IMAGE PROCESSING APPARATUS, CONTROL METHOD THEREOF, AND STORAGE MEDIUM

BACKGROUND OF THE INVENTION

Field of the Invention

This disclosure relates to an image processing apparatus, a control method thereof, and a storage medium.

Description of the Related Art

Emphysema is a type of obstructive pulmonary (lung) disease. After progression of destruction of alveoli mainly caused by cigarette smoking, emphysema exhibits enlargement of airspaces. The number of emphysema patients has been on the rise in recent years.

For tests and diagnoses of emphysema, a method called spirometry, which is for measuring breathing capacity, is mainly used. Spirometry involves measuring the amount of air that is actually inhaled and exhaled. For patients with severe emphysema, this measurement may become painful as the ability to breathe decreases.

Accordingly, quantitative measurements using medical image data (which may hereinafter be also referred to as "CT image") captured by an X-ray computed tomography (CT) apparatus have been proposed in recent years. "Guidelines for the diagnosis and treatment of COPD (chronic obstructive pulmonary disease), 2nd ed., The Japanese Respiratory Society, Medical Review Co., Ltd. (2004)" states that a technique called "Goddard method" in which the stages of emphysema progression are expressed in scores is particularly simple and has been widely used. Therefore, there has been a demand for analysis software that enables evaluation based on the Goddard method.

The evaluation based on the Goddard method uses cross-sections of three lung fields, an upper lung field (near the aortic arch), a middle lung field (at the bronchial bifurcation), and a lower lung field (1 to 3 cm above the diaphragm). For each of the right and left lungs, the ratio of the area of a low attenuation area (LAA) to the area of each of the three lung fields is expressed in a score, and the severity of the chronic obstructive pulmonary disease is determined on the basis of the sum of the resulting scores. Note that the LAA is a region having a CT number clearly lower than that of a normal lung field region in a CT image. Typically, a region having a CT number of −950 HU or less is regarded as an LAA.

The measurements made at the six points on the right and left described above do not fully determine the condition of the entire lungs that are vertically long organs. Besides the score evaluation at the six points described above, it may be necessary to provide a mechanism that allows a diagnostician to visually and intuitively determine how the condition develops in the body axis direction.

SUMMARY OF THE INVENTION

Accordingly, this disclosure provides a mechanism that allows a user to recognize the location where there are many lesions in the entire lung fields.

An image processing apparatus according to the disclosure includes an acquiring unit configured to acquire medical image data of a subject; a first extracting unit configured to extract a lung field region in each of a plurality of tomographic images of the medical image data acquired by the acquiring unit; a second extracting unit configured to extract an emphysema region in the lung field region extracted by the first extracting unit; a calculating unit configured to calculate, for each of the plurality of tomographic images, a ratio of the emphysema region to the lung field region; and a display control unit configured to perform control to display, in a display unit, an image of the medical image data and a value representing the ratio of the emphysema region calculated by the calculating unit such that the value representing the ratio of the emphysema region and a position of the tomographic image corresponding to the value are identifiable.

Further features of the present invention will become apparent from the following description of exemplary embodiments with reference to the attached drawings.

DESCRIPTION OF THE EMBODIMENTS

Embodiments of the present invention will now be described with reference to the drawings.

Figure 1:
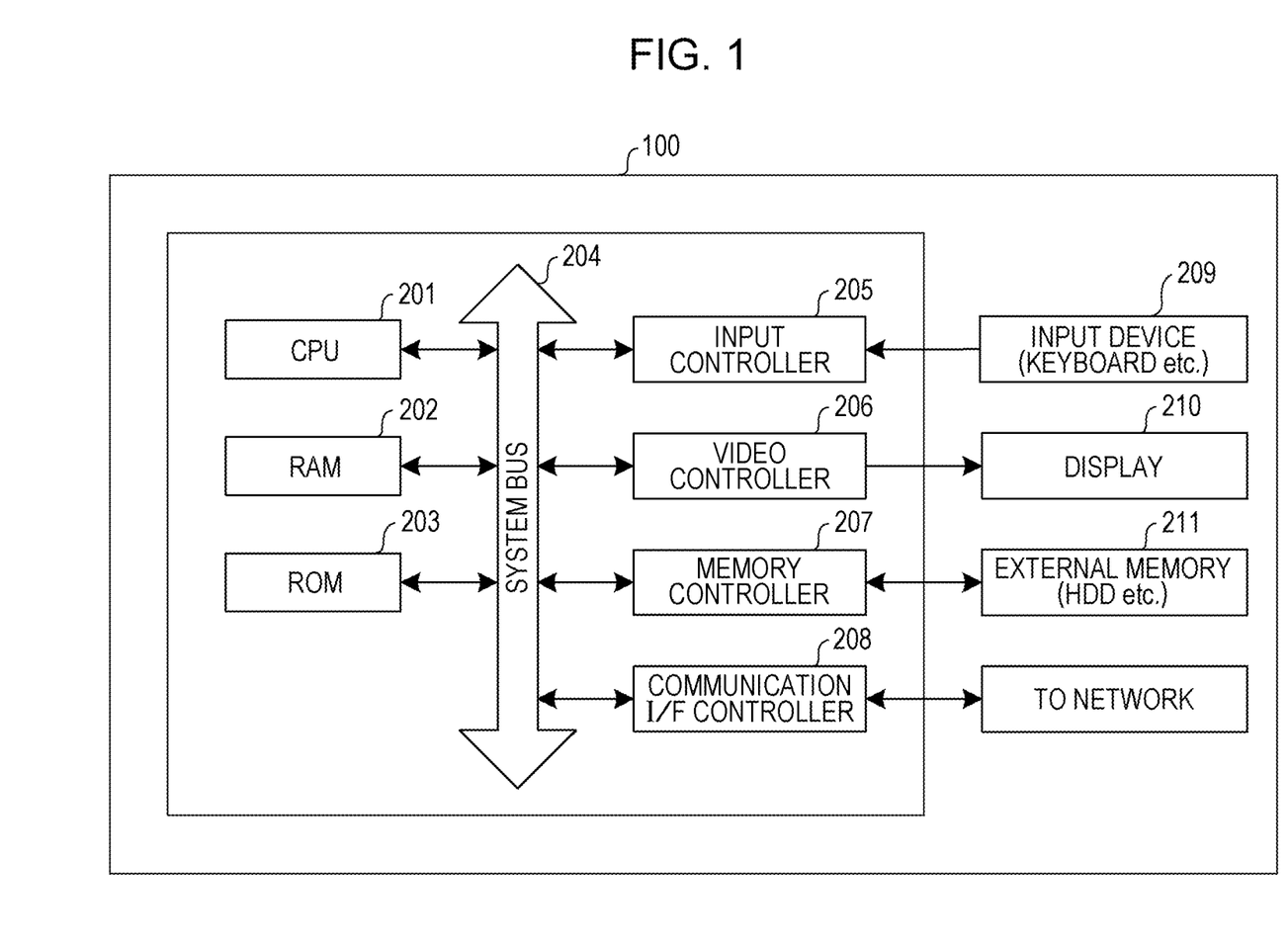
FIG. 1 illustrates a hardware configuration of a medical image processing apparatus according to an embodiment of the present invention.

With reference to FIG. 1, a hardware configuration of a medical image processing apparatus (which may hereinafter be simply referred to as "image processing apparatus") 100 according to an embodiment of the present invention will be described. Note that the hardware configuration of the image processing apparatus 100 illustrated in FIG. 1 is merely an example, and various other configurations are possible depending on the application and purpose of use.

The image processing apparatus 100 includes a central processing unit (CPU) 201, a random-access memory (RAM) 202, a read-only memory (ROM) 203, a system bus 204, an input controller 205, a video controller 206, a memory controller 207, a communication interface (I/F) controller 208, an input device 209, a display 210, and an external memory 211.

The CPU 201 provides comprehensive control over devices and controllers connected to the system bus 204.

The RAM 202 serves as a main memory and a work area for the CPU 201. The CPU 201 loads a program required for execution of processing into the RAM 202 and executes the program, thereby implementing various operations.

The ROM 203 or the external memory 211 stores a basic input/output system (IOS), which is a control program for the CPU 201, an operating system (OS), and various programs required for implementing functions executed by various devices.

The input controller 205 controls an input from the input device 209, such as a keyboard or a pointing device (e.g., mouse).

The video controller 206 controls the display of a display device, such as the display 210. Examples of the display 210 (display unit) include a cathode-ray tube (CRT) and a liquid crystal display.

The memory controller 207 controls access to the external memory 211, such as a hard disk drive (HDD) or flexible disk that stores a boot program, browser software, various applications, font data, user files, and various types of data, or a card-type memory connected to a Personal Computer Memory Card International Association (PCMCIA) card slot via an adapter.

The CPU 201 enables display on the display 210, for example, by expanding (rasterizing) an outline font in a display information region in the RAM 202. Also, the CPU 201 allows a user to give instructions with a mouse cursor (not shown) on the display 210.

Various programs used for the image processing apparatus 100 to execute various types of processing (described below) are stored in the external memory 211. The programs are loaded into the RAM 202 as necessary, and executed by the CPU 201. Definition files, various information tables, and medical images used by a program according to an embodiment of the present invention are stored in the external memory 211. The medical images may be stored, for example, on an external server and acquired therefrom by the image processing apparatus 100.

The description of the hardware configuration of the image processing apparatus 100 illustrated in FIG. 1 ends here.

A functional configuration of the image processing apparatus 100 will now be described with reference to FIG. 2.

The image processing apparatus 100 includes, as functional units, an image acquiring unit 1001, a lung field region extracting unit 1002, an emphysema region extracting unit 1003, a calculating unit 1004, a graph generating unit 1005, and a display control unit 1006. The image acquiring unit 1001 acquires medical image data, such as CT images of a subject captured by a modality. The lung field region extracting unit 1002 extracts a lung field region of the subject on the basis of the medical image data acquired by the image acquiring unit 1001. The emphysema region extracting unit 1003 extracts an emphysema region of the subject on the basis of the medical image data acquired by the image acquiring unit 1001. The calculating unit 1004 calculates, for each medical image data, the ratio of the extracted emphysema region to the extracted lung field region. The graph generating unit 1005 generates a graph that shows the ratio of the emphysema region to the lung field region calculated by the calculating unit 1004 and a subject's position in the medical image data corresponding to the ratio. The display control unit 1006 causes an image of the subject and the graph generated by the graph generating unit 1005 to be displayed on a display screen.

Figure 2:
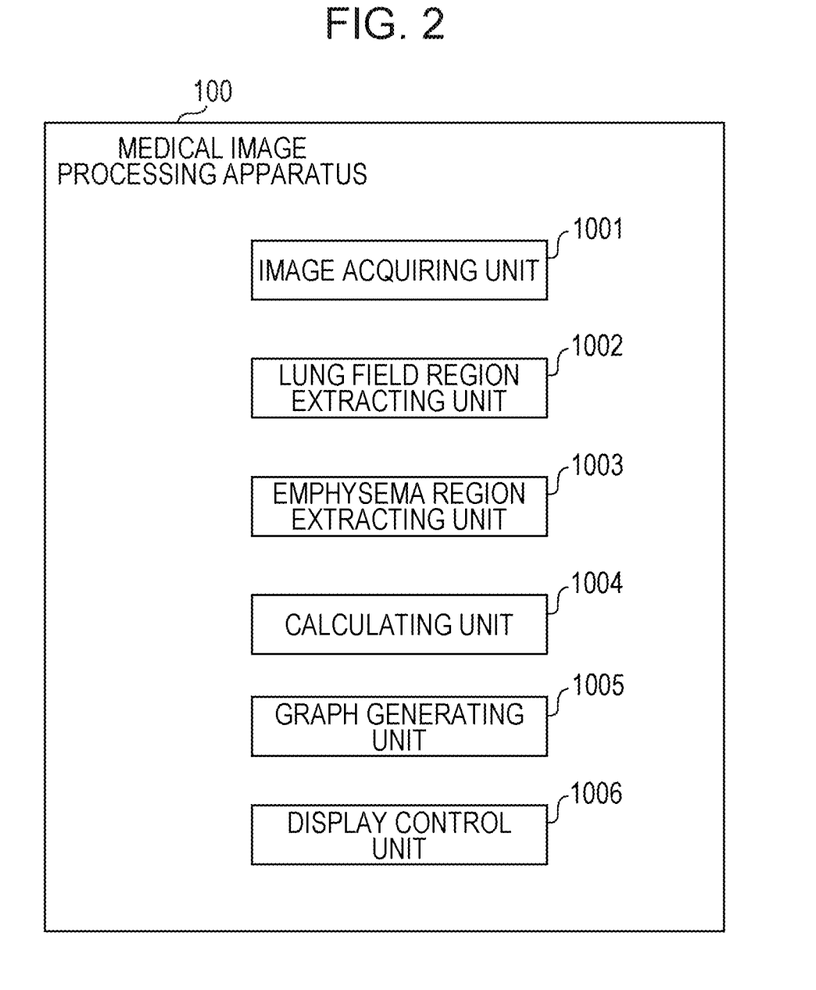
FIG. 2 illustrates a functional configuration of the medical image processing apparatus according to an embodiment of the present invention.

The description of the functional configuration of the image processing apparatus 100 illustrated in FIG. 2 ends here.

Processing according to embodiments of the present invention will now be described in detail with reference to the flowchart of FIG. 3.

First Embodiment

In step S301, the CPU 201 of the image processing apparatus 100 acquires, for example, a group of CT images, which are sliced images (tomographic images) captured by an X-ray CT apparatus. In the field of medicine, images captured by such a modality device are typically transmitted to a picture archiving communication system (PACS) connected to the modality device via a network, and are centrally managed by the PACS. Accordingly, the image processing apparatus 100 is configured such that the images can be acquired not only internally, but also from the PACS. The CPU 201 of the image processing apparatus 100 may acquire not only sliced images, but also resliced images obtained by reslicing a three-dimensional image formed by a plurality of sliced images.

In step S302, the CPU 201 of the image processing apparatus 100 replaces the CT number of a background portion, which is not a human body region in each of the acquired sliced images, with a CT number greater than those corresponding to a lung field region. This is to prevent the background portion from being accidentally extracted during extraction of an emphysema region later on. Specifically, the CT number of the background portion is replaced with −700 HU.

Then, a lung field region is extracted for each sliced image by identifying pixels with CT numbers smaller than a predetermined threshold (e.g., CT number: −400 HU), which is a reference value for extracting a lung field region. The lung field region extracting method is not limited to this. That is, as long as a lung field region can be identified, user's designation of the lung field region may be received or any other method, such as that described in Japanese Patent Laid-Open No. 2003-70781, may be used.

In step S303, the CPU 201 of the image processing apparatus 100 extracts an emphysema region for each of the sliced images acquired in step S301. An emphysematous lesion is extracted as an LAA in the sliced image. More specifically, the emphysema region is extracted by identifying pixels with CT numbers smaller than a known value (e.g., CT number: −900 HU) corresponding to emphysema. The emphysema region extracting method is not limited to this. Any other method, such as that described in Japanese Patent Laid-Open No. 2003-70781, may be used to extract the emphysema region.

In step S304, the CPU 201 of the image processing apparatus 100 calculates, for each sliced image, the ratio of the emphysema region extracted in step S303 to the lung field region extracted in step S302. More specifically, the CPU 201 calculates the ratio by dividing N by M, where M is the number of pixels in the lung field region and N is the number of pixels in the emphysema region. Thus, for each sliced image, the CPU 201 calculates a value representing the ratio of the emphysema region to the lung field region. The calculated value is managed in association with the sliced image.

In step S305, the CPU 201 of the image processing apparatus 100 generates a graph by plotting the value representing the ratio calculated for each sliced image in step S304. The generated graph is a graph 401 shown in FIG.

4. The graph 401 in FIG. 4 has reference lines corresponding to 25%, 50%, and 75%, which are reference values used for score determination in the Goddard method and each representing the ratio of emphysema. In the graph 401 in FIG. 4, a curve segment within the range of emphysema ratios from 0% to less than 25% is shown in blue, a curve segment within the range of emphysema ratios from 25% to less than 50% is shown in orange, a curve segment within the range of emphysema ratios from 50% to less than 75% is shown in white, and a curve segment within the range of emphysema ratios from 75% to less than 100% is shown in red. Thus, by varying the display of the graph stepwise in accordance with the value representing the emphysema ratio, the user can clearly recognize which part of the entire lung fields of the subject is significantly affected by emphysema.

In step S306, the CPU 201 of the image processing apparatus 100 displays, side by side, a coronal cross-sectional image generated by reslicing a three-dimensional image formed by the group of sliced images acquired in step S301 and the graph generated in step S305. As shown in FIG. 4, by displaying a coronal cross-sectional image 402 and the graph 401 side by side on a screen, the user can easily compare a value representing an emphysema ratio with a position in the subject corresponding to the value. That is, the user can identify which position in the subject corresponds to a portion indicating a high emphysema ratio in the graph, and can recognize at a glance the distribution of emphysema which cannot be known only from scores calculated on the basis of the Goddard method.

In step S307, the CPU 201 of the image processing apparatus 100 determines whether a user's selecting operation with the input device 209 (e.g., mouse click) has been received on the graph 401 displayed in step S306. If the CPU 201 determines that the selecting operation has been received, the process proceeds to step S308, and otherwise the process proceeds to step S310.

In step S308, the CPU 201 of the image processing apparatus 100 identifies a position on the graph 401 at which the selecting operation has been received in step S307, and then identifies a sliced image corresponding to a value representing the ratio at the identified position.

In step S309, the CPU 201 of the image processing apparatus 100 displays, in a display region 403 (see FIG. 4), the sliced image identified in step S308. Thus, when the user wants to refer to a sliced image corresponding to a value on the graph 401, the sliced image can be easily displayed on the display screen. After the sliced image is displayed in the display region 403, the process returns to step S307.

In step S310, the CPU 201 of the image processing apparatus 100 determines whether an instruction to enlarge or reduce (i.e., change the display magnification of) the coronal cross-sectional image 402 and an instruction to move the display position of the coronal cross-sectional image 402 have been received from the user. If the instruction to enlarge or reduce and the instruction to move the display position have been received, the process proceeds to step S311, and otherwise the process proceeds to step S312.

In step S311, the CPU 201 of the image processing apparatus 100 changes the display size and the display position of the coronal cross-sectional image 402 in accordance with the user's instructions received in step S310. Then, while maintaining the display size and position of the coronal cross-sectional image 402 changed in accordance with the user's instructions (or in synchronization with changes in the display size and position of the coronal cross-sectional image 402), the CPU 201 changes the display size and position of the graph 401 showing the emphysema ratio.

Figure 6:
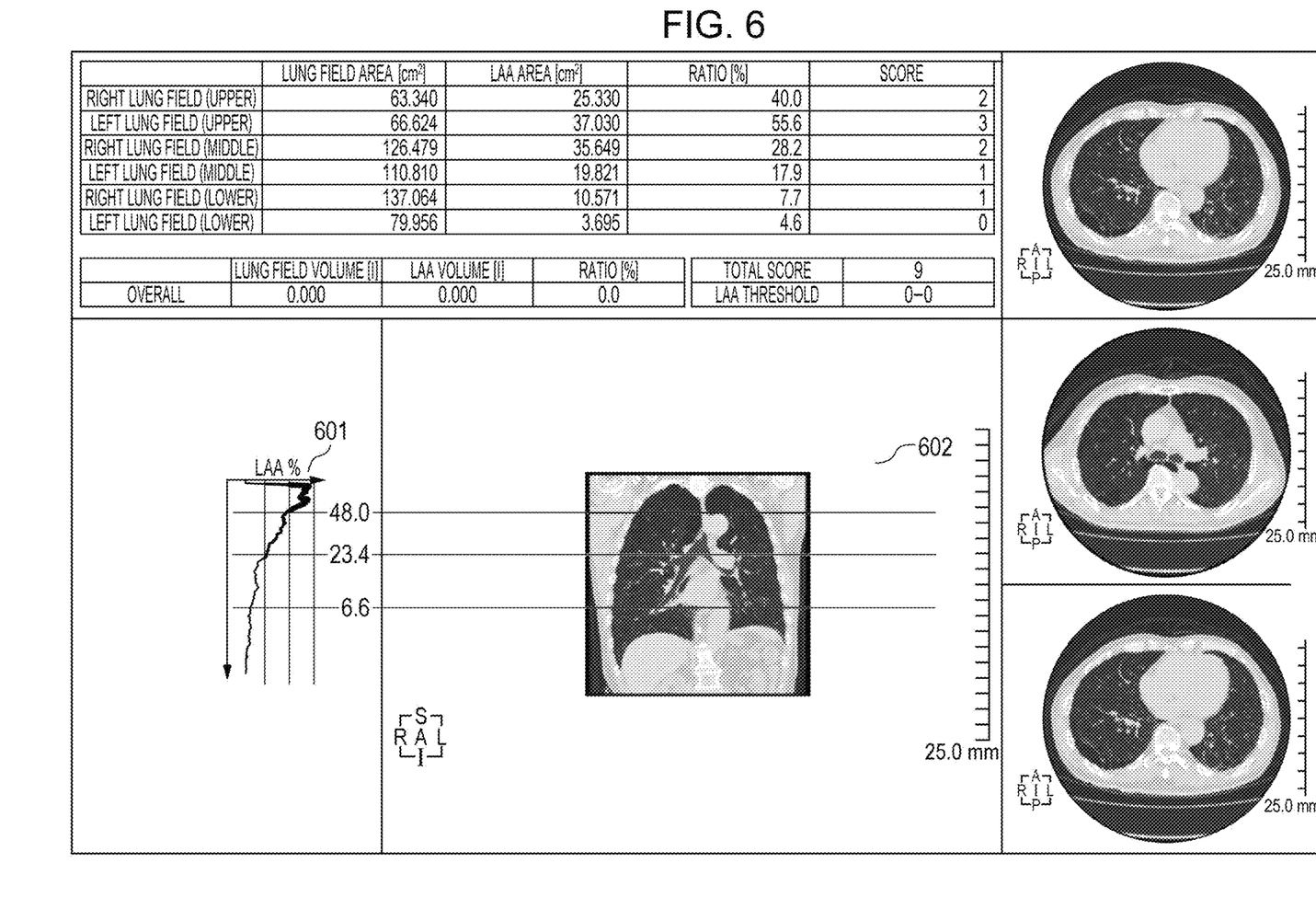
FIG. 6 shows a screen in which an image of medical image data and a graph, which is changed in display size in accordance with a change in the display size of the image, are displayed side by side according to an embodiment of the present invention.

An example will be described with reference to FIG. 6. FIG. 6 shows a screen in which the size of the coronal cross-sectional image 402 in FIG. 4 has been changed. The display size of a coronal cross-sectional image 602 is reduced in accordance with an instruction from the user. The display size of a graph 601 is reduced to the scale of the coronal cross-sectional image 602, with the positional relationship between the graph 601 and the coronal cross-sectional image 602 maintained. Although the coronal cross-sectional image 602 is displayed in a reduced size in the present embodiment, it may of course be displayed in an enlarged size.

Figure 7:
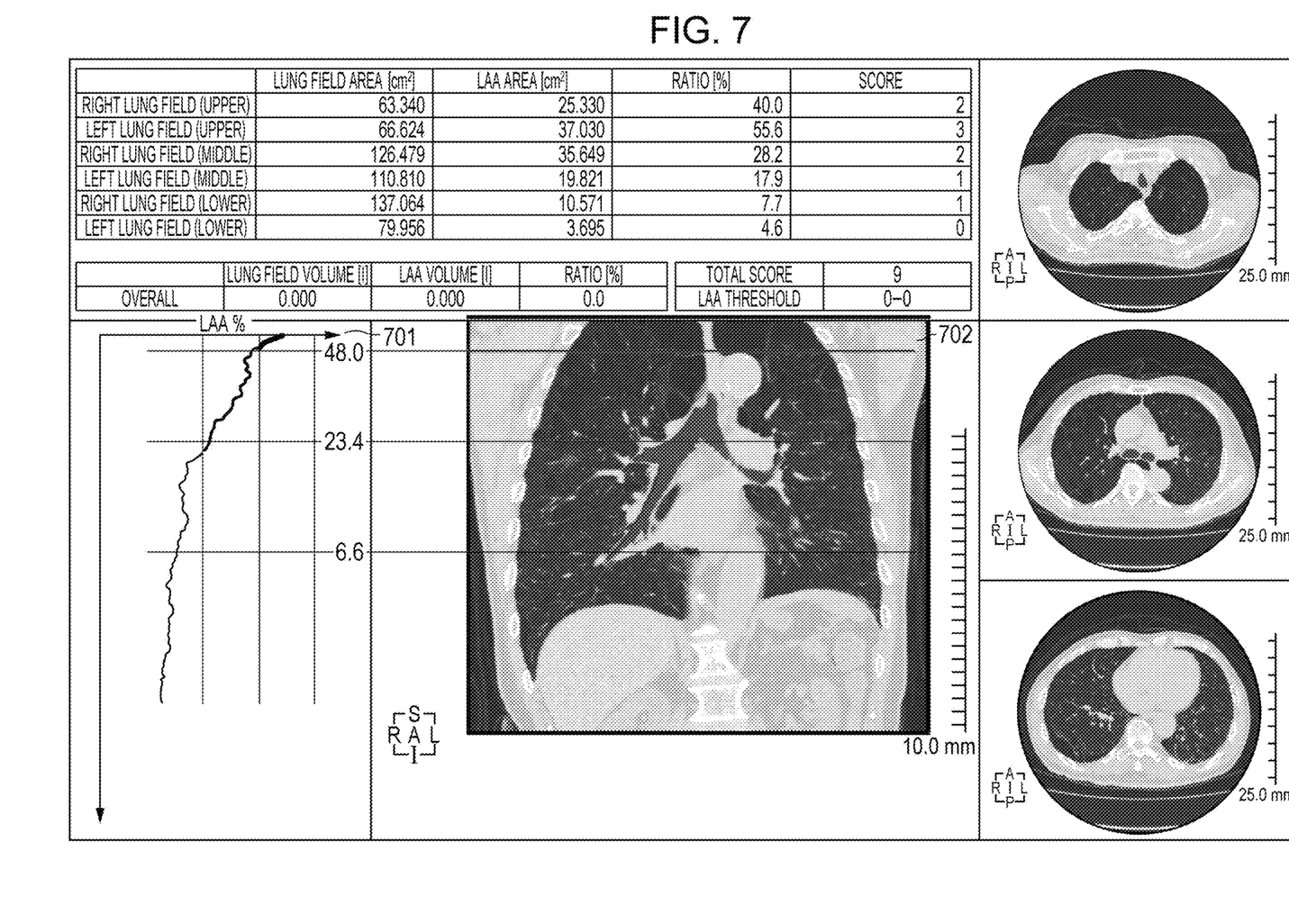
FIG. 7 shows a screen in which an image of medical image data and a graph, which is changed in display position in accordance with movement of the image, are displayed side by side according to an embodiment of the present invention.

FIG. 7 shows a screen in which the position of the coronal cross-sectional image 402 in FIG. 4 has been changed. The display position of a graph 701 is changed in synchronization with the movement of a coronal cross-sectional image 702, with the positional relationship between the graph 701 and the coronal cross-sectional image 702 maintained.

As described above, it is possible not only to change the display size and position of the coronal cross-sectional image, but also to change the display size and position of the graph in synchronization with the coronal cross-sectional image. This allows the user to view the distribution of emphysema in the entire lungs, and to easily understand in detail which part of the lungs is significantly affected by emphysema. In the description above, the display size and position of the coronal cross-sectional image 402 are changed in accordance with the user's instructions received in step S310. Alternatively, the display size and position of the coronal cross-sectional image 402 may be changed in accordance with changes in the display size and position of the graph 401 made in response to receipt of user's instructions.

In step S312, the CPU 201 of the image processing apparatus 100 determines whether an end instruction to end the display has been received from the user. If the CPU 201 determines that the end instruction has been received, the display process ends, and otherwise the process returns to step S307.

Figure 3:
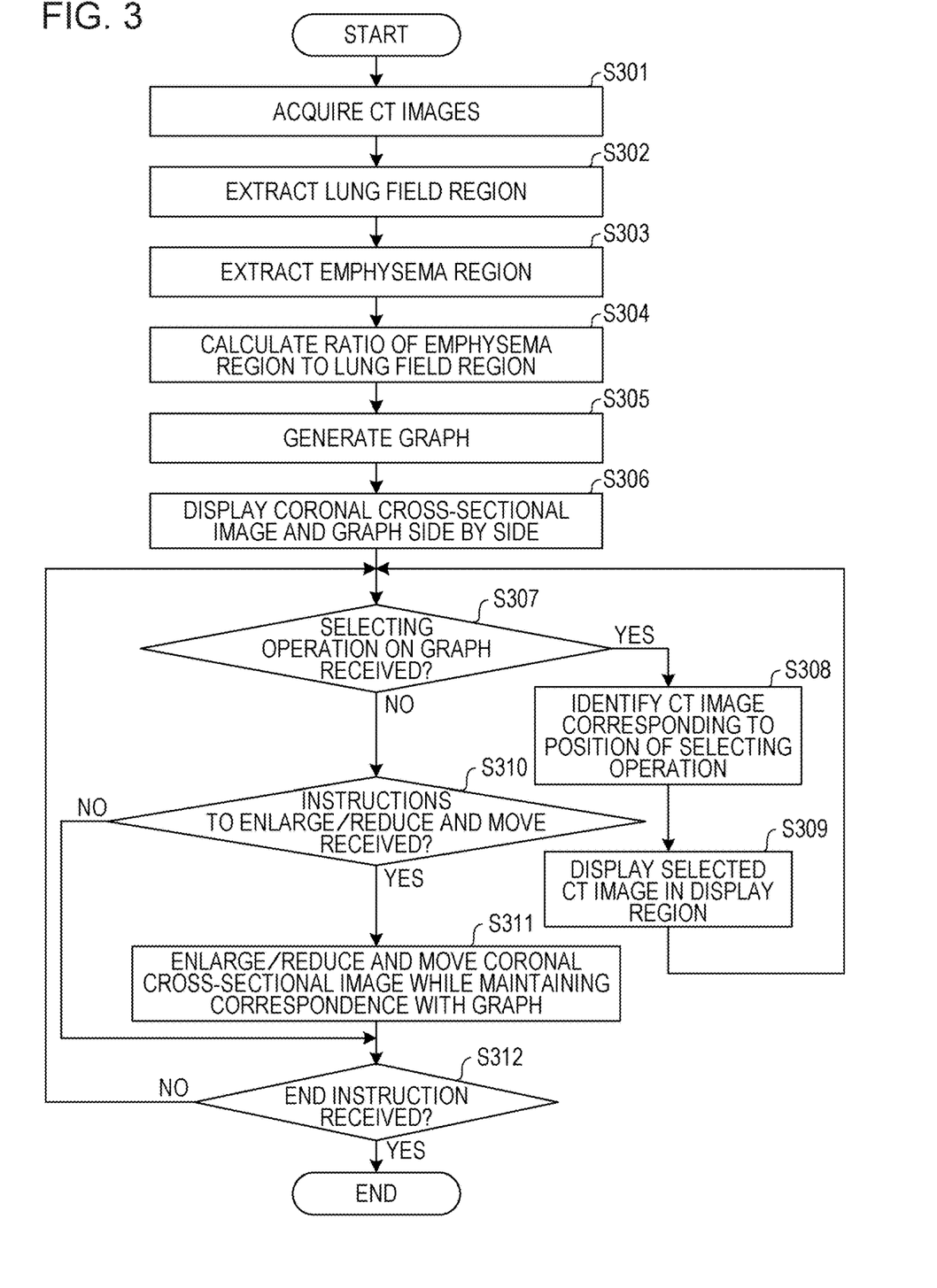
FIG. 3 is a flowchart illustrating a flow of processing according to an embodiment of the present invention.
Figure 4:
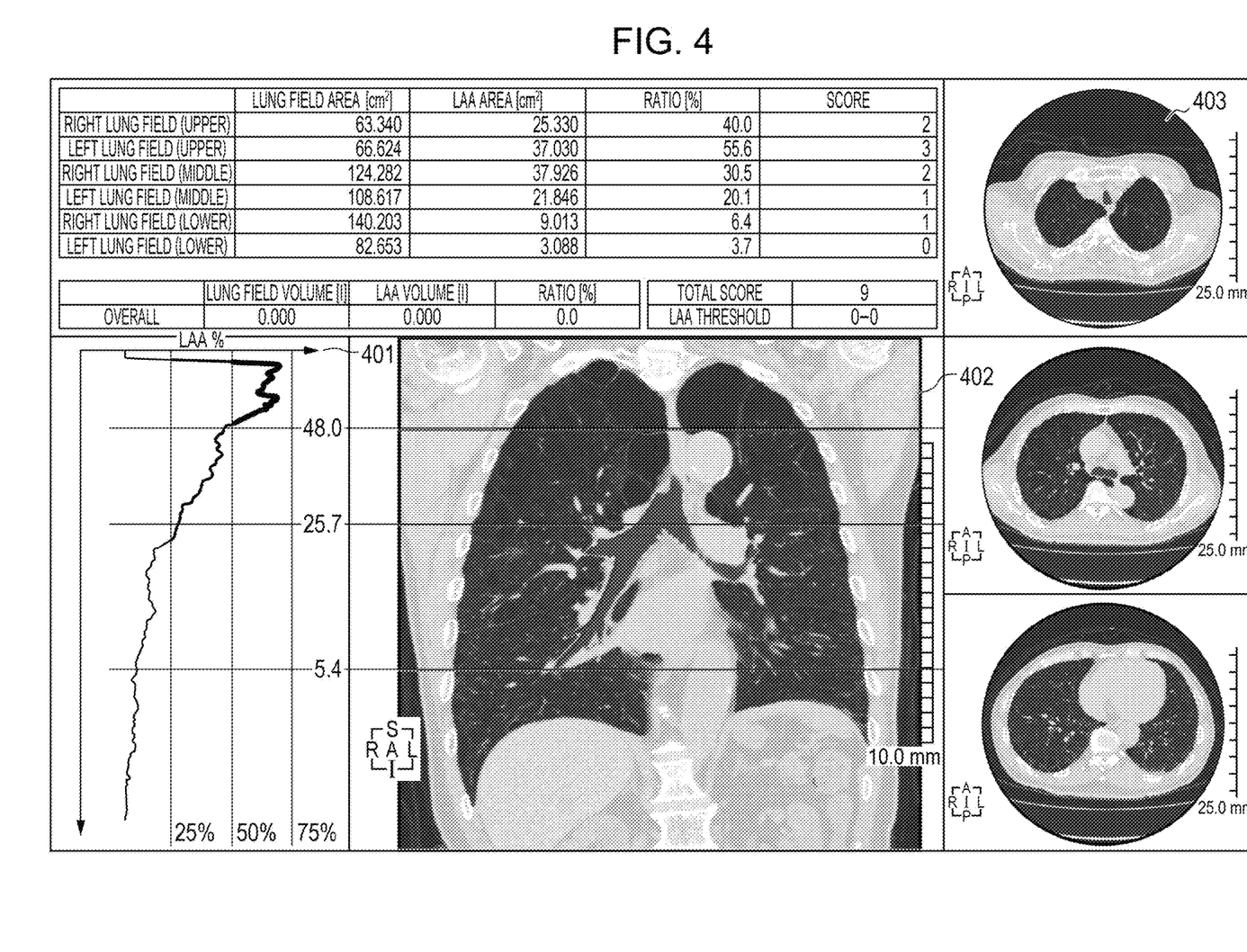
FIG. 4 shows a screen in which an image of medical image data and a graph are displayed side by side according to an embodiment of the present invention.

The description of the flowchart of FIG. 3 ends here.

Second Embodiment

In the first embodiment described above, the lung field region in each sliced image is not divided into right and left lungs, and values each representing the ratio of an emphysema region to the entire lung field region are calculated to generate a graph. In a second embodiment, the lung field region is divided into a right lung field region and a left lung field region. Then, a graph showing values each representing the ratio of a right emphysema region to the right lung field region, and a graph showing values each representing the ratio of a left emphysema region to the left lung field region are generated. The same parts as those of the first embodiment will not be described here, and differences from the first embodiment will be described.

With reference to the flowchart of FIG. 3, only operations different from those in the first embodiment will be described. Operations not described here are performed in the same manner as in the first embodiment.

In step S302, the CPU 201 of the image processing apparatus 100 replaces the CT number of a background portion, which is not a human body region in each of the acquired sliced images, with a CT number greater than those corresponding to a lung field region. This is to prevent the background portion from being accidentally extracted during extraction of an emphysema region later on. Specifically, the CT number of the background portion is replaced with 800 HU.

Then, a lung field region is extracted for each sliced image by identifying pixels with CT numbers smaller than a predetermined threshold (e.g., CT number: −400 HU), which is a reference value for extracting a lung field region. As shown in a display region 503 in FIG. 5, the extracted lung field region includes two regions on the right and left. These regions may be stored as a right lung field region and a left lung field region by receiving user's selections with the mouse, or may be identified as a right lung field region and a left lung field region using a known technique.

In step S303, the CPU 201 of the image processing apparatus 100 extracts a right emphysema region and a left emphysema region in the right lung field region and the left lung field region, respectively, extracted in step S302. The emphysema region extracting method is the same as that in the first embodiment. By carrying out the emphysema region extracting method within the regions extracted in step S302, the right and left emphysema regions in the right and left lung field regions are extracted.

In step S304, the CPU 201 of the image processing apparatus 100 calculates the ratios of the right and left emphysema regions extracted in step S303 to the respective right and left lung field regions.

Figure 5:
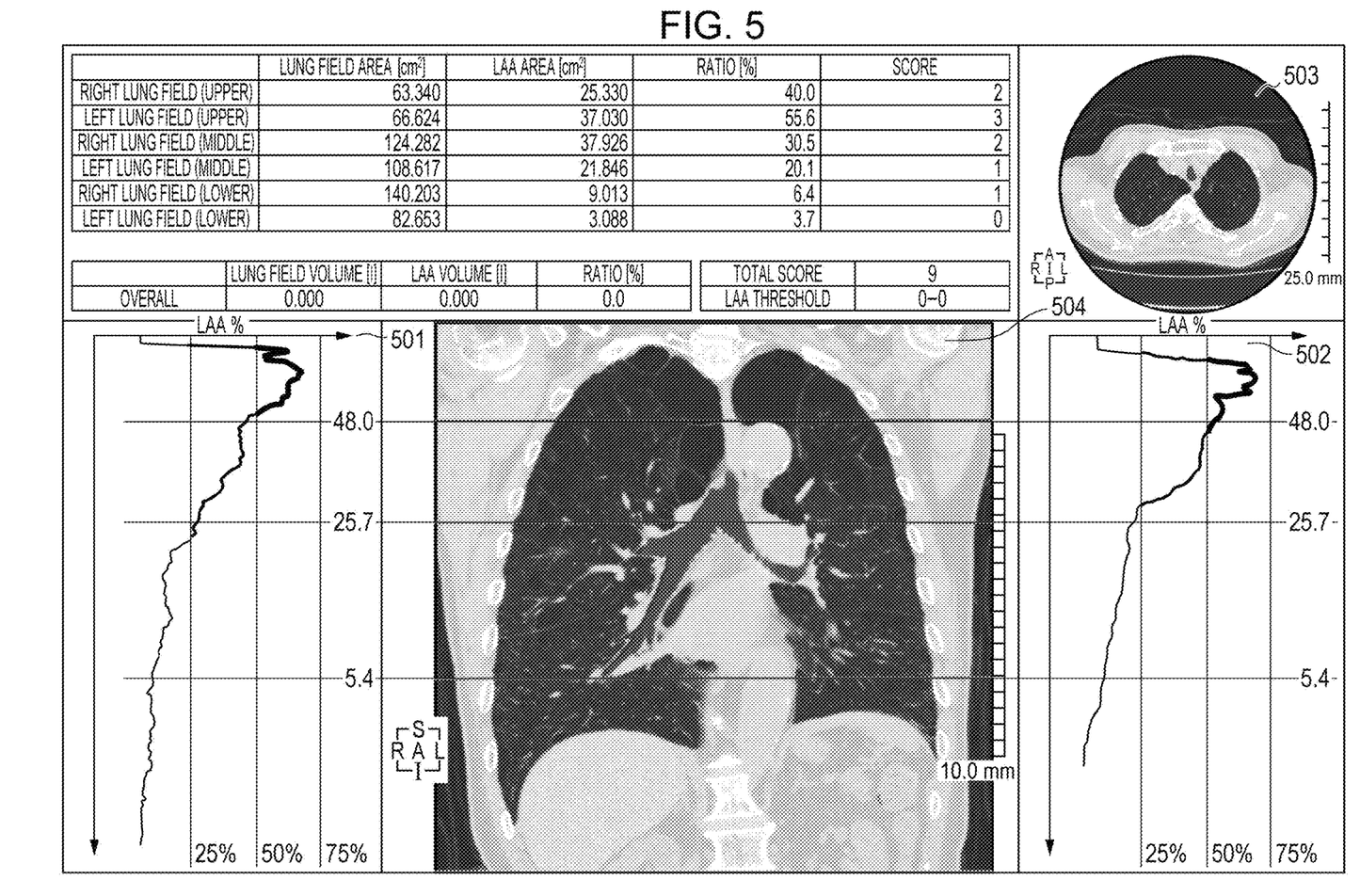
FIG. 5 shows a screen in which an image of medical image data and graphs for right and left lungs are displayed side by side according to an embodiment of the present invention.

In step S305, the CPU 201 of the image processing apparatus 100 generates a graph 501 showing values each representing the ratio of the right emphysema region to the right lung field region, and a graph 502 showing values each representing the ratio of the left emphysema region to the left lung field region, as shown in FIG. 5.

In step S306, the CPU 201 of the image processing apparatus 100 displays the graphs generated in step S305 at the corresponding positions with respect to a coronal cross-sectional image. More specifically, the graph 501 showing values each representing the ratio of the right emphysema region to the right lung field region is displayed adjacent to the right lung field region in a coronal cross-sectional image 504, and the graph 502 showing values each representing the ratio of the left emphysema region to the left lung field region is displayed adjacent to the left lung field region in the coronal cross-sectional image 504. This allows the user to recognize how the emphysema progresses in each of the right lung field region and the left lung field region in the coronal cross-sectional image 504.

The description of the second embodiment ends here.

Third Embodiment

A third embodiment of the present invention will now be described. In the second embodiment, a lung field region is divided into a right lung field region and a left lung field region. Then, a graph showing values each representing the ratio of a right emphysema region to the right lung field region, and a graph showing values each representing the ratio of a left emphysema region to the left lung field region are generated and displayed separately as in FIG. 5. In the third embodiment, the graphs, each showing the ratio of the emphysema region to the corresponding lung field region, are displayed in the same region in a superimposed manner as in FIG. 8. The system configuration, hardware configuration, functional configuration, and data tables of the third embodiment are the same as those of the second embodiment. The same operations as those of the second embodiment will not be described here, and only operations different from those of the second embodiment will be described.

With reference to the flowchart of FIG. 3, a flow of processing according to the third embodiment will be described in detail. The description of steps S301 to S304 will be omitted, as it is the same as that in the second embodiment.

Figure 8:
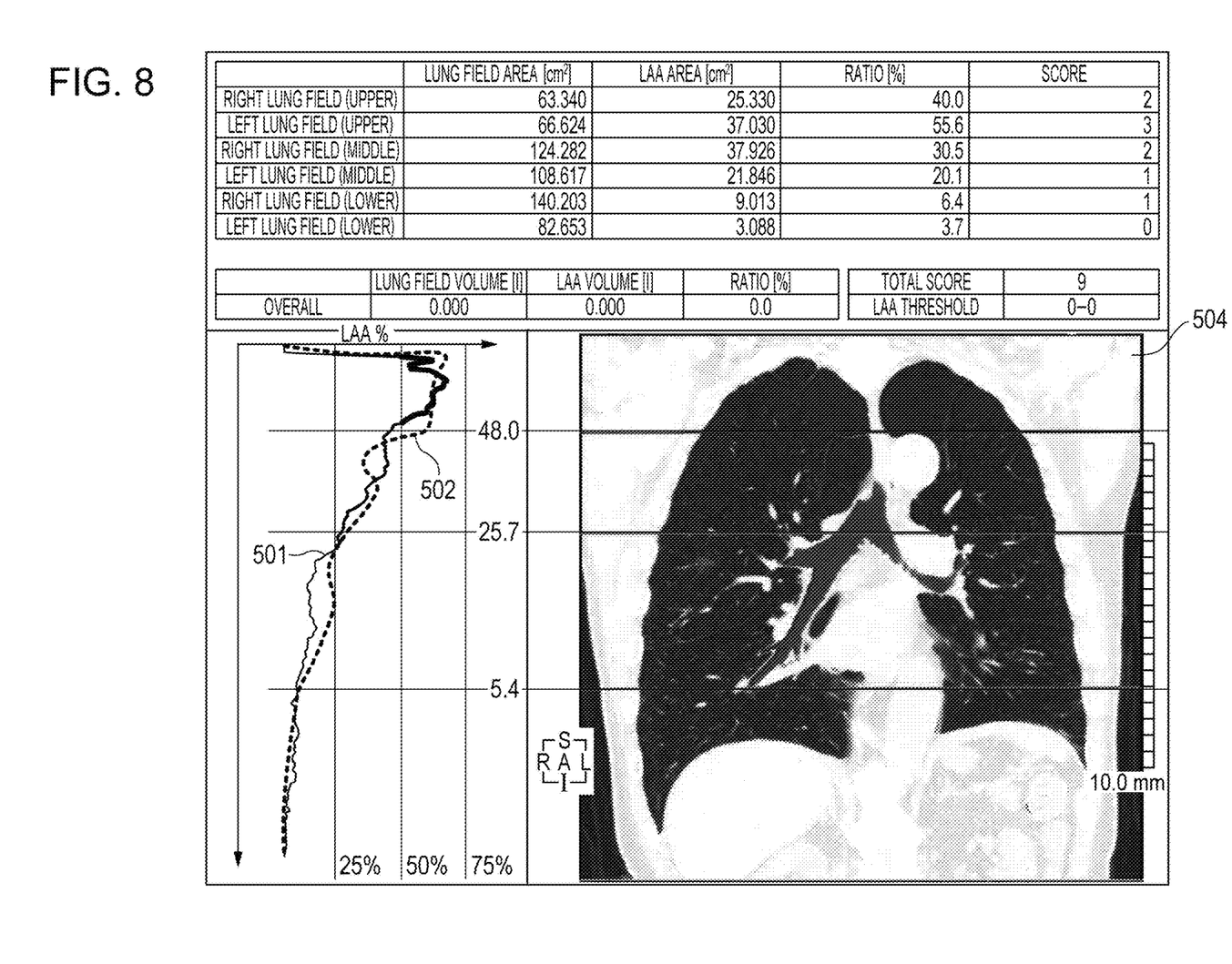
FIG. 8 shows a screen in which an image of medical image data and a graph for both the right and left lungs are displayed according to a third embodiment of the present invention.

In step S305, the CPU 201 of the image processing apparatus 100 generates the graph 501 showing values each representing the ratio of the right emphysema region to the right lung field region, and the graph 502 showing values each representing the ratio of the left emphysema region to the left lung field region, as shown in FIG. 8. The graph 501 and the graph 502 are identifiable, because the graph 501 and the graph 502 are represented by a solid line and a dotted line, respectively, in the present embodiment. Alternatively, the graph 501 and the graph 502 may be displayed in different colors for easy identification.

In step S306, the CPU 201 of the image processing apparatus 100 displays the graph 501 and the graph 502 generated in step S305 such that they positionally correspond to the coronal cross-sectional image 504. In the present embodiment, the graph 501 and the graph 502 are displayed in the same region. A more specific description will be given with reference to FIG. 8.

FIG. 8 shows a screen in which the graph 501 showing values each representing the ratio of the right emphysema region to the right lung field region, and the graph 502 showing values each representing the ratio of the left emphysema region to the left lung field region, are displayed in the same region. As shown, the graph 501 showing the ratio of the right emphysema region to the right lung field region and the graph 502 showing the ratio of the left emphysema region to the left lung field region are displayed in the same region in a superimposed manner. This facilitates comparison of the progression of emphysema between the right lung field region and the left lung field region. This means that the user can intuitively recognize which of the right and left lungs is worse in condition.

The description of the third embodiment ends here.

According to the embodiments of the present invention, the user can understand at a glance the distribution of emphysema (LAA) in the entire lung fields, which cannot be known from scores based on the Goddard method. It is thus possible to allow the user to recognize the degree of progression of subject's symptoms.

In the embodiments of the present invention, a value obtained, for every sliced image forming volume data of the subject captured by the CT apparatus, by calculating the ratio of the emphysema region to the lung field region is used to generate a graph, which is then displayed side by side with an image of the subject. However, the calculation does not necessarily need to be performed for every sliced image forming the volume data. For example, a value obtained once every several sliced images by calculating the ratio of the emphysema region to the lung field region may be used to generate a graph, which is then displayed side by side with an image of the subject.

The present invention may be embodied, for example, as a system, an apparatus, a method, a program, or a storage medium. Specifically, the present invention may be applied to a system composed of a plurality of devices, or to an apparatus composed of a single device. The present invention includes the case of directly or remotely supplying a software program that implements the functions of the above-described embodiments to a system or apparatus. The present invention also includes the case of being achieved when an information processor of the system or apparatus reads out and executes the supplied program code.

Therefore, the program code installed in the information processor for implementing functional processing of the present invention in the information processor also implements the present invention. That is, the present invention also includes a computer program for implementing the functional processing of the present invention.

In this case, the computer program may be object code, a program executed by an interpreter, or script data supplied to an OS, or may be of any other form as long as it has the functions of the program.

Examples of a recording medium for supplying the program include a flexible disk, a hard disk, an optical disc, a magneto-optical disc (MO), a compact disc ROM (CD-ROM), a CD recordable (CD-R), a CD rewritable (CD-RW), a magnetic tape, a nonvolatile memory card, a ROM, and a digital versatile disc (DVD) (DVD-ROM, DVD-R).

The program may be supplied by connecting to a website on the Internet using a browser on a client computer, and then downloading the computer program of the present invention or a compressed file having an automatic installation function, from the website onto a recording medium, such as a hard disk.

The present invention may also be implemented by dividing the program code forming the program of the present invention into multiple files, and downloading the multiple files from different websites. That is, the present invention also includes a World Wide Web (WWW) server that allows multiple users to download program files for implementing the functional processing of the present invention in the information processor.

The program according to the present invention may be encrypted and stored on a storage medium, such as a CD-ROM, and distributed to users. In this case, users satisfying predetermined conditions are permitted to download key information for decrypting the encrypted program from a website via the Internet. By using the downloaded key information, the encrypted program can be executed, installed onto the information processor, and implemented.

The functions of the embodiments described above are implemented when the information processor executes a read-out program. The functions of the embodiments described above may also be implemented when an OS or the like running on the information processor performs part or all of actual processing on the basis of instructions of the program.

The functions of the embodiments described above may also be implemented when the program read out from a recording medium is written to a memory of a function expansion board inserted in the information processor or a function expansion unit connected to the information processor, and then a CPU or the like of the function expansion board or the function expansion unit performs part or all of actual processing on the basis of instructions of the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-213476 filed Oct. 29, 2015 and No. 2016-192784 filed Sep. 30, 2016, which are hereby incorporated by reference herein in their entirety.

What is claimed is:

1. An image processing apparatus comprising:
an acquiring unit configured to acquire medical image data of a subject;
a first extracting unit configured to extract a left lung field region and a right lung region in a plurality of tomographic images of the medical image data acquired by the acquiring unit;
a second extracting unit configured to extract left emphysema region in the left lung field region extracted by the first extracting unit and a right emphysema region in the right lung region extracted by the first extracting unit;
a calculating unit configured to calculate a ratio of the left emphysema region to the left lung field region and ration of the right emphysema region to the right lung region; and
a display control unit configured to perform control to display, in a display unit, the ratio of the left emphysema region to the left lung field region and the ratio of the right emphysema region to the right lung field region.

2. The image processing apparatus according to claim 1, wherein the display control unit performs control such that a value representing the ratio of the left emphysema region and a position of the tomographic image corresponding to the value are displayed side by side in the display unit unit and a value representing the ratio of the right emphysema region and a position of the tomographic image corresponding to the value are displayed side by side in the display unit.

3. The image processing apparatus according to claim 1, further comprising a display position receiving unit configured to receive a change in a display position of the image of the medical image data displayed in the display unit,
wherein the display control unit controls display such that the display position of the image of the medical image data is changed in accordance with the change received by the display position receiving unit, and that a position for displaying the value representing the ratio is also changed to maintain a correspondence with the image of the medical image data.

4. The image processing apparatus according to claim 1, further comprising a display magnification receiving unit configured to receive a change in a display magnification of the image of the medical image data displayed in the display unit,
wherein the display control unit controls display such that the display magnification of the image of the medical image data is changed in accordance with the change received by the display magnification receiving unit, and that a magnification for displaying the value representing the ratio is also changed to maintain a correspondence with the image of the medical image data.

5. The image processing apparatus according to claim 1, wherein the display control unit performs control to display, in the display unit, the image of the medical image data and a value representing the ratio of the left emphysema region calculated by the calculating unit and a value representing the ratio of the right emphysema region calculated by the calculating unit.

6. The image processing apparatus according to claim 1, wherein the value representing the ratio of the left emphysema region and a position of the tomographic image corresponding to the value are identifiable and the value representing the ratio of the right emphysema region and a position of the tomographic image corresponding to the value are identifiable.

7. The image processing apparatus according to claim 1, wherein the image of the medical image data displayed in the display unit is a coronal cross-sectional image.

8. The image processing apparatus according to claim 7, wherein the display control unit performs control such that the value representing the ratio of the left emphysema region and the position of the tomographic image corresponding to the value are displayed side by side in the display unit and a value representing the ratio of the right emphysema region and a position of the tomographic image corresponding to the value are displayed side by side in the display unit.

9. The image processing apparatus according to claim 1, wherein the display control unit performs control such that a value representing the ratio of the left emphysema region is displayed as a first graph generated using the value representing the ratio of the left emphysema region, and a value representing the ratio of the right emphysema region is displayed as a second graph generated using the value representing the ratio of the right emphysema region.

10. The image processing apparatus according to claim 9, wherein the image of the medical image data displayed in the display unit is a coronal cross-sectional image.

11. The image processing apparatus according to claim 9, wherein the display control unit performs control such that the value representing the ratio of the left emphysema region and the position of the tomographic image corresponding to the value are displayed side by side in the display unit and a value representing the ratio of the right emphysema region and a position of the tomographic image corresponding to the value are displayed side by side in the display unit.

12. The image processing apparatus according to claim 9, further comprising a display position receiving unit configured to receive a change in a display position of the image of the medical image data displayed in the display unit,
wherein the display control unit controls display such that the display position of the image of the medical image data is changed in accordance with the change received by the display position receiving unit, and that a position for displaying the value representing the ratio is also changed to maintain a correspondence with the image of the medical image data.

13. The image processing apparatus according to claim 9, wherein the display control unit performs control such that the first graph is displayed differently depending on the value representing the ratio of the right emphysema region and the second graph is displayed differently depending on the value representing the ratio of the left emphysema region.

14. The image processing apparatus according to claim 13, wherein the image of the medical image data displayed in the display unit is a coronal cross-sectional image.

15. The image processing apparatus according to claim 13, wherein the display control unit performs control such that the value representing the ratio of the left emphysema region and the position of the tomographic image corresponding to the value are displayed side by side in the display unit and a value representing the ratio of the right emphysema region and a position of the tomographic image corresponding to the value are displayed side by side in the display unit.

16. The image processing apparatus according to claim 13, further comprising a display position receiving unit configured to receive a change in a display position of the image of the medical image data displayed in the display unit,
wherein the display control unit controls display such that the display position of the image of the medical image data is changed in accordance with the change received by the display position receiving unit, and that a position for displaying the value representing the ratio is also changed to maintain a correspondence with the image of the medical image data.

17. An image processing apparatus comprising:
an acquiring unit configured to acquire medical image data of a subject;
a first extracting unit configured to extract a lung field region in each of a plurality of tomographic images of the medical image data acquired by the acquiring unit;
a second extracting unit configured to extract an emphysema region in the lung field region extracted by the first extracting unit;
a calculating unit configured to calculate, for each of the plurality of tomographic images, a ratio of the emphysema region to the lung field region; and
a display control unit configured to perform control to display, in a display unit, an image of the medical image data and a value representing the ratio of the emphysema region calculated by the calculating unit such that the value representing the ratio of the emphysema region and a position of the tomographic image corresponding to the value are identifiable, wherein the first extracting unit and the second extracting unit extract a left lung field region and a right lung field region, respectively, of the subject;
the calculating unit calculates a ratio of a left emphysema region to the left lung field region extracted by the first extracting unit, and a ratio of a right emphysema region to the right lung field region extracted by the second extracting unit; and
the display control unit performs control such that a value representing the ratio of the left emphysema region and a value representing the ratio of the right emphysema region are separately displayed.

18. A control method of an image processing apparatus, the control method comprising:
an acquiring step of acquiring medical image data of a subject;
a first extracting step of extracting a left lung field region and a right lung region in a plurality of tomographic images of the medical image data acquired in the acquiring step;
a second extracting step of extracting a left emphysema region in the left lung field region and extracting a right emphysema region in the right lung field region extracted in the first extracting step;
a calculating step of calculating a ratio of the left emphysema region to the left lung field region and a ratio of the right emphysema region to the right lung field region; and
a display control step of performing control to display, in a display unit, the ratio of the left emphysema region to the left lung field region and the ratio of the right emphysema region to the right lung field region.

19. A non-transitory storage medium storing a program that causes an image processing apparatus to function as:
an acquiring unit configured to acquire medical image data of a subject;
a first extracting unit configured to extract a left lung field region and a right lung region in a plurality of tomographic images of the medical image data acquired by the acquiring unit;
a second extracting unit configured to extract a left emphysema region in the left lung field region extracted by the first extracting unit and a right emphysema region in the right lung region extracted by the first extracting unit;

a calculating unit configured to calculate a ratio of the left emphysema region to the left lung field region and ration of the right emphysema region to the right lung field region; and a display control unit configured to perform control to display, in a display unit, the ratio of the left emphysema region to the left lung field region and the ratio of the right emphysema region to the right lung field region.

20. An image processing apparatus comprising:

an acquiring unit configured to acquire medical image data of a subject;

a first extracting unit configured to extract a lung field region in each of a plurality of tomographic images of the medical image data acquired by the acquiring unit;

a second extracting unit configured to extract an emphysema region in the lung field region extracted by the first extracting unit;

a calculating unit configured to calculate, for each of the plurality of tomographic images, a ratio of the emphysema region to the lung field region; and a display control unit configured to perform control to display, in a display unit, an image of the medical image data and a value representing the ratio of the emphysema region calculated by the calculating unit such that the value representing the ratio of the emphysema region and a position of the tomographic image corresponding to the value are identifiable, wherein the first extracting unit and the second extracting unit extract a left lung field region and a right lung field region, respectively, of the subject;

the calculating unit calculates a ratio of a left emphysema region to the left lung field region extracted by the first extracting unit, and a ratio of a right emphysema region to the right lung field region extracted by the second extracting unit; and the display control unit performs control such that the ratio of the left emphysema region to the left lung field region and the ratio of the right emphysema region to the right lung field region are displayed on the same graph.

* * * * *